United States Patent [19]

Tiberi et al.

[11] Patent Number: 5,215,915
[45] Date of Patent: Jun. 1, 1993

[54] CLONED GENE ENCODING RAT $D_{1B}$ DOPAMINE RECEPTOR

[75] Inventors: Mario Tiberi; Keith R. Jarvie; Marc G. Caron, all of Durham, N.C.

[73] Assignee: Duke University, Durham, N.C.

[21] Appl. No.: 686,591

[22] Filed: Apr. 16, 1991

[51] Int. Cl.$^5$ .................. C12N 15/12; C12N 15/63
[52] U.S. Cl. ....................... 435/252.3; 435/320.1; 536/23.5; 536/24.31; 536/24.3 B
[58] Field of Search .............. 435/252.3, 320.1; 530/350; 536/27; 436/500

[56] References Cited

FOREIGN PATENT DOCUMENTS

WO90/05780  5/1990  PCT Int'l Appl.
WO91/06557  5/1991  PCT Int'l Appl.

OTHER PUBLICATIONS

Science 237; 268–275, Jul. 17, 1987, Arriza et al. Cloning of Human Mineralocorticoid Receptor ComplementaryDNA: Structural and Functional Kinship with the Glucocorticoid Receptor.
Nature 329: 836–838, Oct. 29, 1987, Masu et al. cDNA cloning of bovine substance-K receptor through oocyte expression system.
Nature 347:72–76, Sep. 6, 1990, Dearry et al. Molecular Cloning and expression of the gene for a human $D_1$, dopamine receptor.
Nature 347:76–80, Sep. 6, 1990, Zhou et al. Cloning and expression of human and rat $D_1$ dopamaine receptors.
Nature 347:80–83, Sep. 6, 1990, Sunahara et al. Human dopamine $D_1$ receptor encoded by an intronless gene on Chromosone 5.
PNAS87:2196–2200, Mar. 1990, Mahan et al. Expression of striatal $D_1$ dopamine receptors coupled to inositol phosphate production and $Ca^{2+}$ mobilization in xenopus oocytes.
F. Monsma et al., Proc. Natl. Acad. Sci. USA 87, 6723–6727 (1990). Sep.
P. Sokoloff et al., Nature 347, 146–151 (1990). Sep. 13.
G. Sheppard The Synaptic Organization of the Brain 2d Ed., 268–288, 308–337 (1979).
M. Tiberi et al., Proc. Natl. Acad. Sci. USA 88, 7491–7495 (1991).

Primary Examiner—David L. Lacey
Assistant Examiner—John D. Ulm
Attorney, Agent, or Firm—Bell, Seltzer, Park & Gibson

[57] ABSTRACT

Disclosed is isolated DNA encoding a $D_{1B}$-dopamine receptor selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor Vectors and host cells containing the same, assay procedures employing $D_{1B}$-dopamine receptors, oligonucleotide probes for identifying $D_{1B}$-dopamine receptors, and isolated and purified $D_{1B}$-dopamine receptors are also disclosed.

15 Claims, 2 Drawing Sheets

CLONED GENE ENCODING RAT $D_{1B}$ DOPAMINE RECEPTOR

This invention was made with Government support under Grant No. NS19576 from the National Institutes of Health. The Government may have certain rights to this invention.

BACKGROUND OF THE INVENTION

Dopamine exerts its physiological actions in the periphery as well as in the central nervous system (CNS) by interacting with multiple dopaminergic receptors. Recently, molecular biological approaches have established that the effects of dopamine in the CNS are mediated by at least three different receptors, namely $D_1$, $D_2$ and $D_3$. See A. Dearry et al., *Nature* 347, 72-76 (1990); Q.-Y. Zhou et al., *Nature* 347, 76-80 (1990); R. Sunahara et al., *Nature* 347, 80-83 (1990); F. Monsma et al., *Proc. Natl. Acad. Sci. USA* 87, 6723-6727 (1990); J. Bunzow et al., *Nature* 336, 783-787 (1988); B. Giros et al., *Nature* 342, 923-926 (1989); F. Monsma, et al., *Nature* 342, 926-929 (1989); P. Sokoloff et al., *Nature* 347, 146-151 (1990). The genes encoding these receptors are distinct but homologous and belong to the large family of receptors coupled to guanine nucleotide regulatory protein (G protein). See B. O'Dowd et al., *Ann. Rev. Neurosci.* 12, 67-83 (1989). One major feature of these receptors is that they contain seven putative membrane spanning domains in their structure.

The actions of dopamine were originally thought to be mediated by an interaction with two distinct receptor subtypes: $D_1$ receptors which were coupled to the stimulation of adenylyl cyclase and $D_2$ receptors which were either uncoupled or coupled to the inhibition of adenylyl cyclase See J. Kebabian and D. Calne, *Nature* 277, 93-96 (1979). More recently, it has become apparent that multiple $D_1$ receptors may exist. See P. Andersen et al., *Trends Pharmacol. Sci.* 11, 231-236 (1990). For instance, it has been demonstrated that injection of rat striatal mRNA into Xenopus oocytes directs the expression of a $D_1$ dopamine receptor coupled to activation of phospholipase C and this activation leads to inositol phosphate (IPs) accumulation in injected eggs. L. Mahan et al., *Proc. Natl. Acad. Sci. USA* 87, 2196-2200 (1990). Furthermore, dopamine does not stimulate adenylyl cyclase in the amygdala, a tissue known to contain specific binding sites for the radiolabeled $D_1$-selective antagonist SCH 23390. P. Andersen et al., supra. In the periphery, $D_1$ receptors have been shown to stimulate adenylyl cyclase as well as phospholipase C. See E. Baldi et al., *Eur. J. Pharmacol.* 149, 351-356 (1988); C. Missale et al., *J. Cardiovasc. Pharmacol.* 11, 643-650 (1985); C. Felder et al., *J. Pharmacol. Exp. Ther.* 248, 171-175 (1989). Moreover, peripheral $D_1$ receptors differ pharmacologically from their CNS counterparts. Using the cloned human $D_1$ receptor as a probe, we have reported that multiple hybridizing bands on Southern blot analysis at low stringency could be observed. This finding is consistent with the presence of other closely related receptors. A. Dearry et al., supra.

In the patent literature, a cloned gene encoding a mammalian $D_2$-dopamine receptor is reported in O. Civelli et al., PCT Patent Application WO 90/05780. A cloned gene encoding a mammalian $D_1$-dopamine receptor is described in J. Bunzow et al., Pending U.S. patent application Ser. No. 07/583,852, filed Sep. 17, 1990. Insofar as these applicants are aware, no distinct subtypes of $D_1$-dopamine receptors have previously been disclosed.

SUMMARY OF THE INVENTION

We now report the cloning of a new $D_1$ receptor subtype, the $D_{1B}$-dopamine receptor, which is strikingly different from the previously cloned $D_1$ receptor in its mRNA distribution.

A first aspect of the present invention is isolated DNA encoding a $D_{1B}$-dopamine receptor selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor.

A second aspect of the present invention is a recombinant DNA sequence comprising vector DNA and a DNA encoding a $D_{1B}$-dopamine receptor as given above.

A third aspect of the present invention is a host cell containing a recombinant DNA sequence as given above.

A fourth aspect of the present invention is an aqueous solution containing cell membranes, said cell membranes containing a $D_{1B}$-dopamine receptor, wherein said cell membranes are free of $D_{1A}$-dopamine receptors. The cell membranes may further contain adenylyl cyclase, with the $D_{1B}$-dopamine receptors capable of stimulating the adenylyl cyclase on binding a $D_{1B}$-dopamine receptor agonist. The cell membranes are also preferably provided free of $D_2$-dopamine receptors and any other dopamine receptor subtypes.

A fifth aspect of the present invention is an assay procedure comprising the steps of, first, providing an aqueous solution containing cell membranes as given above; then adding a test compound to the aqueous solution; and then monitoring the binding of the test compound to the $D_{1A}$ dopamine receptors.

A sixth aspect of the present invention is an oligonucleotide probe capable of selectively hybridizing to a DNA comprising a portion of a gene coding for a $D_{1B}$-dopamine receptor, which probe does not hybridize to a gene coding for a $D_{1A}$-dopamine receptor.

A seventh aspect of the present invention is isolated and purified $D_{1B}$-dopamine receptor which is coded for by DNA selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor.

Figure 1:
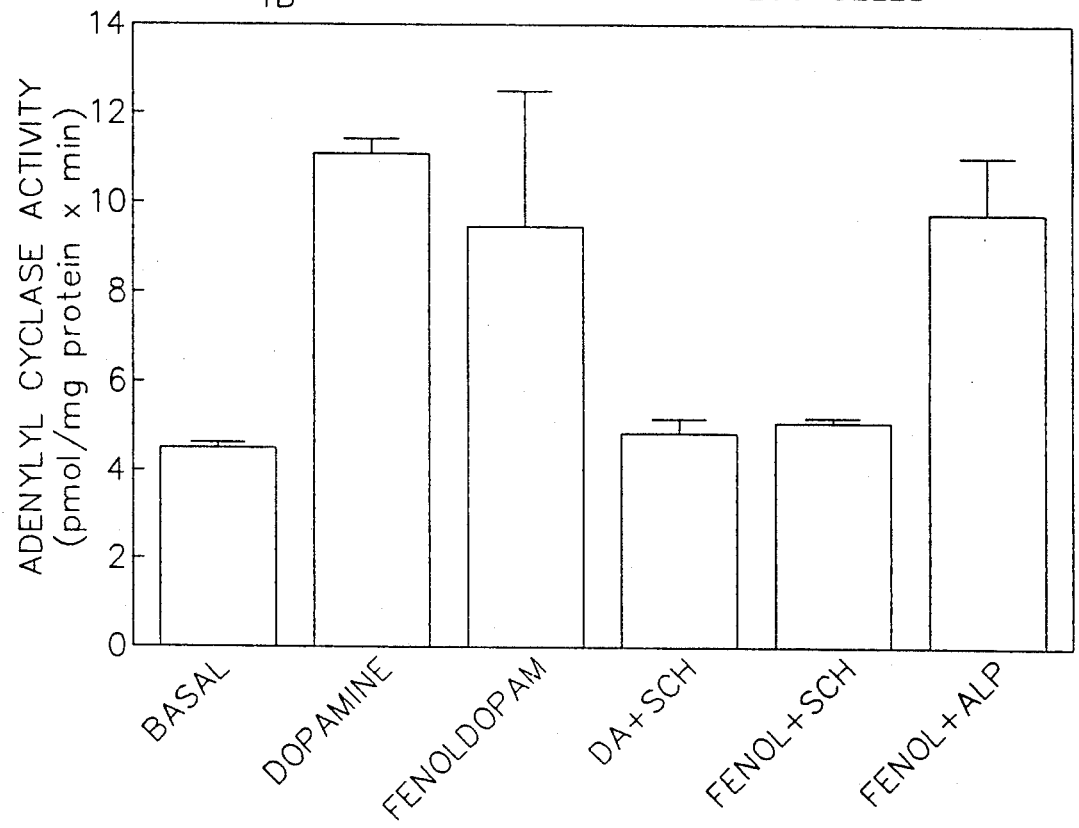
FIG. 1. Stimulation of adenylyl cyclase in membranes prepared from 293 cells transfected with pCMV5-DR5 expression construct. Results are the mean±s.e.m. of a representative example of two independent experiments done in triplicate determinations. Drugs and concentrations used are dopamine (DA), 100 μM; fenoldopam (FENOL), 1 μM; SCH 23390 (SCH), 1 μM; and alprenolol (ALP), 1 μM.

DR5 or $\alpha_{1B}$-adrenergic receptor clone were prelabeled overnight with [$^3$H]myo-inositol. Cells were then incubated for 30 min at 37° C. in absence (basal) or presence (stimulated) of agonist. Dopamine (100 µM) was used to elicit a response in cells transfected either with pCMV5 alone or pCMV5-DR5. Norepinephrine (10 µM) was used to stimulate IPs metabolism in cells transfected with the $\alpha_{1B}$-receptor clone. The results shown as mean±s.e.m., are representative of two independent experiments done in triplicate.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference).

$D_{1B}$-dopamine receptors of the present invention include proteins homologous to, and having essentially the same biological properties as, the protein coded for by the nucleotide sequence set forth as SEQ ID NO:3. This definition is intended to encompass natural allelic variations in the $D_{1B}$-dopamine receptor sequence, but to exclude the $D_{1A}$-dopamine receptor sequence. Cloned genes of the present invention may code for $D_{1B}$-dopamine receptors of any species of origin, including mouse, rat, rabbit, cat, and human, but preferably code for receptors of mammalian origin. Thus, DNA sequences which hybridize to the sequence given in SEQ ID NO:3 and which code for expression of a $D_{1B}$-dopamine receptor are also an aspect of this invention. Conditions which will permit other DNA sequences which code for expression of a $D_{1B}$-dopamine receptor to hybridize to the sequence given in SEQ ID NO:3 can be determined in a routine manner. Further, DNA sequences which code for polypeptides coded for by the sequence given in SEQ ID NO:3, or sequences which hybridize thereto and code for a $D_{1B}$ receptor, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

The production of cloned genes, recombinant DNA, vectors, host cells, proteins and protein fragments by genetic engineering techniques is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

DNA which encodes the $D_{1B}$-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the $D_{1B}$-dopamine receptor gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, $D_{1B}$-dopamine receptor gene sequences may be recovered by use of the polymerase chain reaction (PCR) procedure, with the PCR oligonucleotide primers being produced from the $D_{1B}$-dopamine receptor gene sequence provided herein. See U.S. Pat. Nos. 4,683,195 to Mullis et al. and U.S. Pat. No. 4,683,202 to Mullis.

The $D_{1B}$-dopamine receptor may be synthesized in host cells transformed with vectors containing DNA encoding the $D_{1B}$-dopamine receptor. A vector is a replicable DNA construct. Vectors are used herein either to amplify DNA encoding the $D_{1B}$-dopamine receptor and/or to express DNA which encodes the $D_{1B}$-dopamine receptor An expression vector is a replicable DNA construct in which a DNA sequence encoding the $D_{1B}$ receptor is operably linked to suitable control sequences capable of effecting the expression of the $D_{1B}$ receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the $D_{1B}$ receptor vectors constructed using recombinant DNA techniques. Transformed host cells ordinarily express the $D_{1B}$ receptor, but host cells transformed for purposes of cloning or amplifying the $D_{1B}$ receptor DNA need not express the $D_{1B}$ receptor. When expressed, the $D_{1B}$ receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and *Serratia marcesans* are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the $D_{1B}$ receptor in plasmid or viral vectors (Siebenlist et al., *Cell* 20, 269 (1980)). The promoter and Shine-Dalgarno sequence (for prokaryotic host expression) are operably linked to the DNA encoding the $D_{1B}$ receptor, i.e., they are positioned so as to promote transcription of the Ds receptor messenger RNA from the DNA.

Eukaryotic microbes such as yeast cultures may be transformed with suitable $D_{1B}$ receptor-encoding vectors. See, e.g., U.S. Pat. No. 4,745,057. *Saccharomyces cerevsiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the $D_{1B}$ receptor, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 27, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes may also be ligated into the expression vector 3' of the the $D_{1B}$ receptor coding sequences to provide polyadenylation and termination of the mRNA.

Cultures of cells derived from multicellular organisms are a desirable host for recombinant $D_{1B}$-dopamine receptor synthesis. In principal, any higher eukaryotic cell culture is workable, whether from vertebrate or invertebrate culture, including insect cells. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the human genomic $D_{1B}$ receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the $D_{1B}$ receptor DNA. An example of a suitable selectable marker is dihydrofolate reductase (DHFR) or thymidine kinase. See U.S. Pat. No.

4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

$D_{1B}$-dopamine receptors made from cloned genes in accordance with the present invention may be used for screening compounds for $D_{1B}$ dopamine receptor activity, or for determining the amount of a dopaminergic drug in a solution (e.g., blood plasma or serum). For example, host cells may be transformed with a vector of the present invention, $D_{1B}$-dopamine receptors expressed in that host, the cells lysed, and the membranes from those cells used to screen compounds for $D_{1B}$-dopamine receptor binding activity. Competitive binding assays in which such procedures may be carried out are well known, as illustrated by the Examples below. By selection of host cells which do not ordinarily express a dopamine receptor, preparations free of $D_{1A}$ receptors, $D_2$ receptors, and other dopamine receptor subtypes can be obtained. Further, $D_{1B}$-dopamine receptor agonists and antagonists can be identified by transforming host cells with vectors of the present invention, which host cells also express adenylyl cyclase. Membranes obtained from such cells can be used in biochemical studies wherein the activity of the adenylyl cyclase is monitored. $D_{1B}$ receptor agonists will stimulate the adenylyl cyclase. Such cells must be capable of operatively associating the $D_{1B}$-dopamine receptor with the adenylyl cyclase, i.e., G protein must also be present in the cell membranes. Procedures for carrying out assays such as these are also described in greater detail in the Examples which follow.

Cloned genes and vectors of the present invention are useful in molecular biology to transform cells which do not ordinarily express the $D_{1B}$-dopamine receptor to thereafter express this receptor. Such cells are useful as intermediates for making cell membrane preparations useful for receptor binding assays, which are in turn useful for drug screening. Further, genes and vectors of the present invention are useful in gene therapy. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out by homologous recombination or site-directed mutagenesis See generally K. Thomas and M. Capecchi, *Cell* 51, 503–512 (1987); W. Bertling, *Bioscience Reports* 7, 107–112 (1987); O. Smithies et al., *Nature* 317, 230–234 (1985).

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing $D_{1B}$-receptor gene expression in various tissues. For example, tissue can be probed in situ with oligonucleotide probes carrying detectable groups by conventional autoradiography techniques to investigate native expression of this receptor or pathological conditions relating thereto (e.g., human genetic disorders). This can be done routinely by temperature gradient electrophoresis. In addition, oligonucleotides of the present invention can be used to probe for other $D_{1B}$ receptors or $D_{1B}$ receptors in other species. Further, chromosomes can be probed to investigate the presence or absence of a $D_{1B}$-dopamine receptor gene, and potential pathological conditions related thereto.

Isolated and purified $D_{1B}$-dopamine receptor of the present invention is useful in the rational design of drugs which interact with this receptor. The $D_{1B}$ receptor may be purified from cell membranes or lysed cell fractions containing the receptor, as described above, in accordance with known procedures, including column chromatography (e.g., ion exchange, gel filtration, electrophoresis, affinity chromatography, etc.), optionally followed by crystallization See generally Enzyme Purification and Related Techniques, *Methods in Enzymology* 22, 233–577 (1977)

The present invention is explained in greater detail in the following examples. These examples are intended to be illustrative of the present invention, and should not be construed as limiting thereof. In the examples, bp means base pair(s); Kb means kilobase; w/v means weight/volume; hr means hour; sec means second; cm$^2$ means square centimeters; μg means micrograms; μl means microliters; ml means milliliters; mmol means millimoles; nM means nanomolar; μM means micromolar; mM means millimolar; M means Molar; Ci means curies; GBq means gigabecquerels; and temperatures are given in degrees centigrade.

EXAMPLE 1

Polymerase Chain Reaction (PCR) Cloning

Degenerate primers corresponding to the 5th (5'AACCATGGATCCTACATCCCTGTGGCCAT-CATGATTGTCACNTA 3') (SEQ ID NO:1) and 6th (5'CCNCACAAACACACGACAACCGATG-GAAAGAAGCTTAAG ATCAAT 3') (SEQ ID NO:2) transmembrane (TM) regions of the human $D_1$ dopamine receptor described in A. Dearry et al., supra, were used in the polymerase chain reaction (PCR) to amplify sheared human genomic DNA. The PCR products were subcloned into the sequencing vector pBluescript II SK+(Stratagene), identified by colony lifts using end-labeled oligonucleotides corresponding to TM regions of the human $D_1$ receptor and sequenced using the dideoxy chain termination method as discussed below. One of these products (V-15; 230 bp) displayed a significant homology with the human $D_1$ receptor and corresponded to the 5th TM region, the 3rd intracellular loop and the 6th TM region.

EXAMPLE 2

Genomic Library Screening

The V-15 clone noted in Example 1 above was used as a template for the synthesis of a [$^{32}$P]-labeled probe by PCR. At the end of the reaction, the labeled probe was purified on a Sephadex G-50 column (NICK column; Pharmacia). The purified probe was used to screen 1.5×10⁶ recombinants of a rat testis genomic library in λDASH II. Duplicate nylon filters (Biotrans membranes, ICN) were hybridized in a buffer containing 5×SSC (0.75M sodium chloride, 0.075M sodium citrate; pH 7.0), 5×Denhardt's solution (0.1% (w/v) Ficoll, 0.1% (w/v) polyvinylpyrrolidone and 0.1% (w/v) bovine serum albumin), 0.05M sodium phosphate (pH 7.0), 0.1% SDS, 50% formamide, 200 µg per ml of sheared salmon sperm DNA, and [$^{32}$P]-labeled V-15 probe (1×10⁶ cpm per ml) at 42° C. for 18-22 hr. At the end of the hybridization period, filters were first washed in a solution containing 2×SSC (0.30M sodium chloride, 0.03M sodium citrate; pH 7.0) and 0.1% SDS at room temperature and then washed at 50° C. in a solution containing 0.1×SSC (0.015M sodium chloride, 0.0015M sodium citrate, pH 7.0) and 0.1% SDS. Filters were then exposed overnight at −70° C. on Kodak X-OMAT films.

EXAMPLE 3

DNA Sequencing

Nucleotide sequencing of both DNA strands was done according to the dideoxy chain termination method (F. Sanger et al., *Proc. Natl. Acad. Sci. USA* 74, 5463-5467 (1977)) by primer extension in pBluescript II SK+ with T7 DNA polymerase (Pharmacia) and $^{35}$S-labeled nucleotide premix ($^{35}$Sequetide; New England Nuclear; Boston, Mass.).

Several clones were isolated and processed for plaque purification using this procedure. A 4.2 kb EcoRI restriction fragment from one clone (DR5) had an open reading frame of 1425 bp (475 aa) which contained the full coding sequence. The calculated molecular weight of this protein is 52834 Da. The nucleotide and predicted amino acid sequence are given together in SEQ ID NO:3, and the predicted amino acid sequence is given seperately in SEQ ID NO:4. The putative initiator methionine was selected on the basis of the best Kozak consensus sequence found in frame with the remainder of the coding block and preceded by a stop codon.

COMPARATIVE EXAMPLE A

Structural Comparison with Prior D₁ Receptors

Hydropathicity analysis of DR5 (SEQ ID NO:3) revealed the presence of seven stretches of hydrophobic amino acids (data not shown) that may correspond to the seven TM regions typical of G protein-coupled receptors. See B. O'Dowd et al., *Ann. Rev. Neurosci.* 12, 67-83 (1989). At the amino acid level, this putative receptor has about 50% overall identity with the prior art rat and human D₁ dopamine receptor. Within TM regions, the DR5 clone has 80% identity with this D₁ receptor, whereas the amino and carboxy termini are the most divergent regions (<20% identity). In the TM regions of the rat D₂ and D₃ dopamine receptors, this identity is only 47% and 39% respectively. Furthermore, two serine residues (Ser 224 and Ser 227) in the 5th TM region and an aspartate residue (Asp 118) in the 3rd TM region are present in this putative receptor, as they are in every cloned catecholamine receptor. These residues have been postulated to be involved in the interaction with the catechol hydroxyl and amino groups of the catecholamines. Putative sites for N-linked glycosylation are found in the amino terminus (asparagine 7) and the 2nd extracellular domain (asparagine 194). A cysteine residue (at position 370) is found in the carboxy tail near the 7th TM region. This residue is conserved in most of the G protein-coupled receptors and has been demonstrated in the $\beta_2$-adrenergic and rhodopsin receptors to be palmitoylated.

EXAMPLE 4

Expression in Kidney Cells

An expression construct was prepared using the pCMV5 expression vector (B. Cullen, *Methods Enzymol.* 152, 684-704 (1987)) and a 4.2 kb EcoRI restriction fragment of rat clone DR5 (SEQ ID NO:3). African green monkey kidney (COS-7) cells were transiently transfected with the pCMV5DR5 expression construct by the DEAE-Dextran procedure. B. Cullen, supra. Human embryonic kidney (293) cells were transiently transfected using a calcium-phosphate transfection system (Bethesda Research Laboratories Life Technologies, Inc.).

EXAMPLE 5

Ligand Binding Analysis

Cis-flupentixol, cis-piflutixol, cis-teflutixol were obtained from Lundbeck (Denmark). Fluperlapine was from Novo Nordisk (Bagsvaerd, Denmark). SCH 23388 AND SCH 23390 were obtained from Schering Plough (Bloomfield, N.J.). Apomorphine, (+)butaclamol, dopamine hydrochloride, haloperidol, R(−)- propylnorapomorphine (NPA) and spiperone were purchased from Research Biochemical Industries (RBI). Fenoldopam and SKF 38393 were obtained from Smith, Kline & French. [$^{125}$I]SCH 23982 was from New England Nuclear Boston, Mass.).

COS-7 cells were harvested 48 to 72 hr after transfection. Cells contained in culture flasks (75 cm²) were rinsed with 5 ml of lysis buffer (10 mM Tris-HCl, 5 mM EDTA, pH 7.4). Cells were then scraped and homogenized in lysis buffer for 15 sec using a Brinkman homogenizer. Membranes were centrifuged at 50,000×Gravity for 20 min and the pellet was resuspended in binding buffer (50 mM Tris-HCl, 100 mM NaCl, 5 mM EDTA, pH 7.4). Saturation binding studies were performed with increasing concentrations of [$^{125}$I]SCH 23982 (2200 Ci/mmol; 1 Ci=37 GBq). Competition curves were performed with increasing concentrations of unlabeled drug under study against a constant concentration of [$^{125}$I]SCH 233982 (~0.20 nM). The reaction was initiated by adding 100 µl of membranes (~0.45 µg protein) and the assay mixture was incubated in a final volume of 200 µl for 1 hr at room temperature. Assay mixtures were then vacuum-filtered through Whatman GF/C glassfiber filters and washed 3 times with 5 ml of cold washing buffer (50 mM Tris-HCl, 100 mM NaCl, pH 7.2). Total and nonspecific binding were delineated in the absence and presence of 10 µM cis-flupentixol. Each determination was done in triplicate. Bound radioactivity was measured at an efficiency of 75% using a gamma counter (LKB instruments). Binding curves were analyzed using non-linear multiple regression programs. See A. DeLean et al., *Mol. Pharmacol.* 21, 5-16 (1982); G. McPherson, *J. Pharmacol. Methods* 14, 213-228 (1985).

In membranes prepared from COS-7 cells transfected with pCMV5-DR5, the D receptor antagonist [$^{125}$I]SCH 23982 was bound to one homogeneous class of binding sites with a dissociation constant ($K_D$) of 0.41±0.01 nM (n=3). This value is similar to the $K_D$ value for this ligand (0.35±0.02 nM, n=2) obtained when the same cells are transfected with the previously characterized $D_1$ dopamine receptor clone (pCMV5-D construct). See A. Dearry et al., Nature 347, 72-76 (1990). In untransfected or mock transfected COS-7 cells, little or no specific binding was observed. Table 1 summarizes the binding affinities of dopaminergic antagonists and agonists for the binding of [$^{125}$I]SCH 23982 in membranes prepared from COS-7 transfected either with pCMV5-DR5 or pCMV5-$D_1$. The results show that the pharmacological profile at the rat receptor (DR5 clone) is closely related to that observed for the prior human $D_1$ dopamine receptor (the $D_{1A}$ receptor).

TABLE 1

Equilibrium dissociation constant values ($K_D$) of doparminergic compounds for [$^{125}$I]SCH 23982 binding in COS-7 cell membranes.

| | HUMAN $D_{1A}$ RECEPTOR (nM) | RAT $D_{1B}$ RECEPTOR (nM) | $D_{1B}/D_{1A}$ |
|---|---|---|---|
| ANTAGONISTS | | | |
| SCH 23390 | 0.17 | 0.11 | 0.6 |
| CIS-PIFLUTIXOL | 0.65 | 2 | 3.1 |
| (+)BUTACLAMOL | 1 | 6 | 6.0 |
| CIS-FLUPENTIXOL | 4 | 7 | 1.8 |
| SCH 23388 | 15 | 10 | 0.7 |
| HALOPERIDOL | 24 | 35 | 1.5 |
| CIS-TEFLUTIXOL | 24 | 37 | 1.5 |
| FLUPERLAPINE | 75 | 510 | 6.8 |
| SPIPERONE | 450 | 2600 | 5.8 |
| AGONISTS | | | |
| FENOLDOPAM | 17 | 11 | 0.6 |
| SKF 38393 | 135 | 100 | 0.7 |
| APOMORPHINE | 360 | 240 | 0.7 |
| NPA | 1540 | 1050 | 0.7 |
| DOPAMINE | 12000 | 3900 | 0.3 |

Binding parameters shown are the result of two independent experiments conducted in triplicate determinations. For each drug, the two competition curves were co-analyzed and fitted to a one-site model.

The binding at both receptors was stereoselective since SCH 23390 was about 100 times more potent than SCH 23388. In general, antagonists seemed to be slightly less potent at the rat receptor (DR5 clone) while the agonists appeared to display slightly higher affinities for the rat receptor.

EXAMPLE 6

Adenylyl Cyclase Activity

Adenylyl cyclase activity in 293 cells was measured 72 hr after the transfection. Crude membranes from transfected 293 cells were prepared and resuspended to ~1.25 mg protein/ml in a buffer containing 75 mM Tris-HCl (pH 7.2), 5 mM $MgCl_2$, and 2 mM EDTA (pH 8.0). Adenylyl cyclase activity was assayed in a final volume of 50 μl according to the method previously described. See Y. Salomon et al., Analyt. Biochem. 58, 541-548 (1974).

In 293 cells transiently transfected with the pCMV5-DR5 construct, dopamine and the $D_1$ selective agonist fenoldopam stimulate adenylyl cyclase activity by 2-3 fold (FIG. 1). This effect is blocked by the D1 selective antagonist SCH 23990 but not by the β-adrenergic antagonist alprenolol or the $D_2$ selective antagonist raclopride ($10^{-6}$ M; data not shown). The agonist SKF 38393 ($10^{-6}$ M) also increased the enzyme activity by about twofold.

EXAMPLE 7

Figure 2:
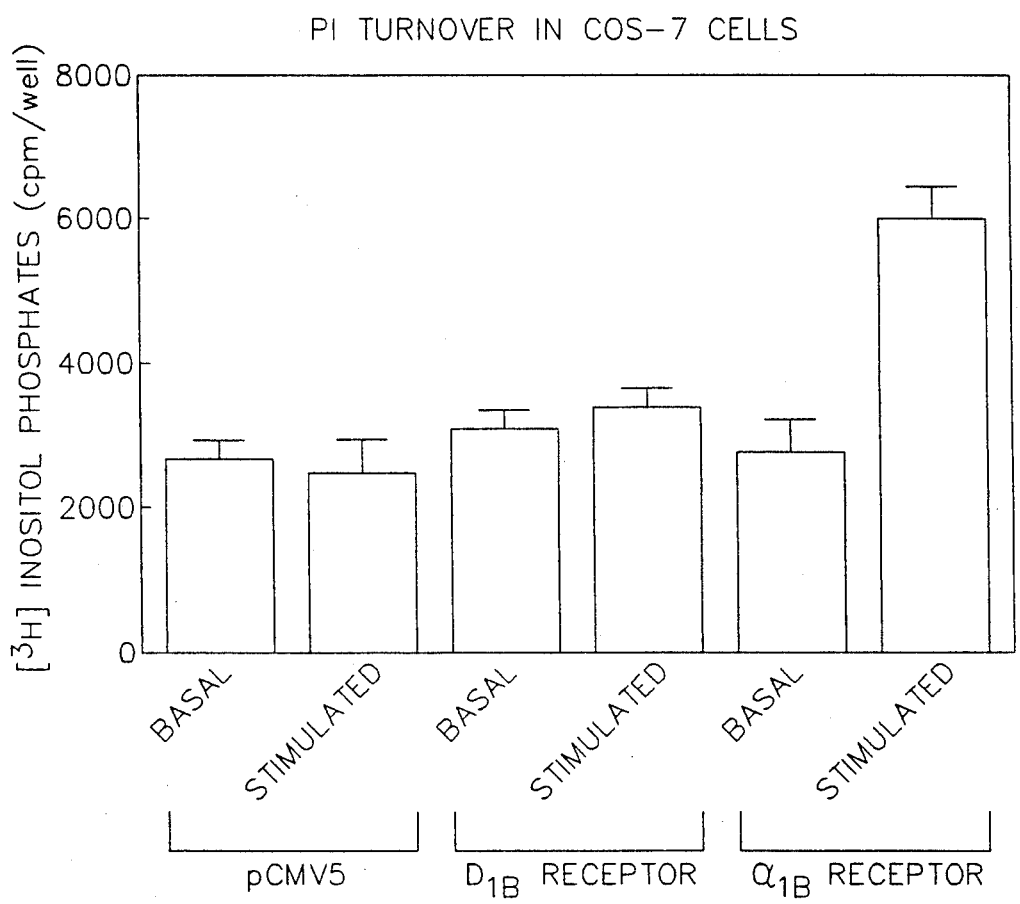
FIG. 2. Inositol phosphate turnover in COS-7 cells. COS-7 cells transfected with pCMV5 alone, pCMV5-

Phosphatidylinositol Turnover 48 hr after transfection, COS-7 cells were labeled overnight with [$^3$H]myo-inositol (18.3 Ci/mmol). [$^3$H]IPs accumulation was assayed as previously described in S. Cotecchia et al., J. Biol. Chem. 265, 63-69 (1990). Dopamine did not stimulate IPs turnover in COS-7 cells transiently transfected with the pCMV5-DR5 construct whereas norepinephrine increased IPs metabolism by about 200% in the same cells transfected with the $\alpha_{1b}$-adrenergic receptor clone (FIG. 2). See S. Cotecchia et al., Proc. Natl. Acad. Sci. USA 85 7159-7163 (1988).

These results, coupled with those of Example 6, demonstrate that the rat clone DR5 encodes a G protein-coupled receptor which is pharmacologically and biochemically similar to that of the previously cloned $D_1$ dopamine receptor. On this basis we proposed that this receptor be referred to as the $D_{1B}$ subtype whereas the previously cloned D receptor would be referred to as the $D_{1A}$ subtype.

EXAMPLE 8

Distribution of $D_{1B}$ Receptor mRNA

Northern Blot Analysis. Poly(A)+RNA was isolated from Sprague-Dawley rat tissues according to the method of Badley et al., Biotechnique 6, 114-116 (1988). The RNA was fractionated by electrophoresis on a 1.2% agarose gel containing formaldehyde, transferred onto nylon membranes by capillary blotting, and then hybridized with a specific [$^{32}$P]-labeled probe.

In Situ Hybridization. A 4.2-kb EcoRI restriction fragment from DR5 clone was subcloned into pBluescript II SK+. [$^{35}$S]-Labeled antisense or sense strand RNA probes were prepared by in vitro transcription and rat brain sections were hybridized as previously described. See R. Fremeau et al., Science 234, 1265-1269 (1986).

In order to determine the distribution of the $D_{1B}$ receptor mRNA, situ hybridization, PCR and standard northern blot analyses were carried out in the manner described above. In situ hybridization revealed that this novel $D_1$ dopamine receptor has a distinct mRNA distribution from the one observed for $D_{1A}$ or $D_2$ receptors in rat brain (data not shown). Prominent labeling was found in the lateral mammilary nuclei, the anterior pretectal nuclei and in several layers of the hippocampus. In contrast, no message was detected in striatum, nucleus accumbens and olfactory tubercle; regions in which $D_{1A}$ receptor mRNA is abundant. Furthermore, in the substantia nigra, a region in which $D_2$ receptor mRNA is present, little signal was found for the $D_{1A}$ and $D_{1B}$ receptors. Northern blot analysis of rat tissues revealed two hybridizing bands in hippocampus with estimated sizes of 3.0 and 3.7 kb (data not shown). These two mRNAs are likely derived from the $D_{1B}$ receptor gene since these bands remained even after extensive high-stringency washings (data not shown), and are both distinct from the message for $D_{1A}$ dopamine receptor which has a mRNA size of 4.2 kb. See A. Dearry et al., supra. PCR methodology was used to amplify a specific 339-bp fragment spanning the end of the coding block and 3' untranslated region of the $D_{1B}$ receptor message to detect mRNA that might be present in low abundance in other rat tissues. Consistent with in situ localization, amplified products were detected in the hippocampus and the hypothalamus (data not shown). In the striatum and the cerebellum a weak signal was observed while in the cortex little or no detectable product was amplified. Furthermore, no detectable products were amplified in kidney, heart, lung and liver tissues.

COMPARATIVE EXAMPLE B

Pharmacological and Functional Comparison

The pharmacological and functional characterization of the rat genomic clone DR5 (SEQ ID NO:3) reveal that this gene encodes a G protein-coupled receptor which represents a distinct $D_1$ receptor subtype from the previously cloned rat and human $D_1$ receptors. See A. Dearry et al., Nature 347, 72–76 (1990); Q.Y. Zhou et al., Nature 347, 76–80 (1990). This receptor is referred to as the $D_{1B}$ subtype whereas the previously characterized $D_1$ receptor is referred to as the $D_{1A}$ subtype. Structurally these two receptors are highly homologous, but differ in their amino and carboxy termini as well as in their extracellular and intracellular loops. Phosphorylation of G protein-coupled receptors has been proposed to be important in the regulation of responsiveness of these receptor systems. Comparison of the sequence of the $D_{1A}$ and $D_{1B}$ receptors reveal that, like the $D_{1A}$ receptor which contains several consensus phophorylation sites for protein kinase A (PKA), protein kinase C (PKC) and receptor kinases in every intracellular loop and the carboxy tail, the $D_{1B}$ receptor contains one consensus PKC site in the first intracellular loop, and one and two consensus PKA sites respectively in the 2nd and 3rd cytoplasmic loop. In addition, potential phosphorylation sites for specific receptor kinases exist on the cytoplasmic regions of this receptor.

A distinguishing property of the $D_{1B}$ dopamine receptor is its restricted CNS distribution. The $D_{1A}$ receptor is synthesized most prominently in the striatum, nucleus accumbens, and olfactory tubercle and to a lesser extent in the limbic, cortical, and hypothalamic areas. In contrast, the $D_{1B}$ receptor is expressed in several cell layers of the hippocampus and in two specific sets of nuclei (hypothalamic lateral mammilary and anterior pretectal). This localization implies that this receptor may play a role in the visual relay system, and in the integration of sensory perception. Moreover, the abundance of the mRNA in the hippocampus may suggest a role in memory function.

Heterogeneity within subfamilies of G protein-coupled receptor has been documented for the adrenergic, serotonergic and muscarinic receptors. This multiplicity has been based on distinct pharmacological properties, signal transduction mechanisms, and differences in tissue distribution. As stated before, several lines of evidence had suggested the existence of dopamine receptor subtypes. However, the concept of multiple CNS $D_1$ dopamine receptor subtypes coupled to adenylyl cyclase had not been advanced. Indeed, using the dopamine ligands currently available, this novel receptor subtype could not have been detected previously on the basis of pharmacological properties.

The foregoing examples are illustrative of the present invention, and are not to be construed as limiting thereof. The invention is defined by the following claims, with equivalents of the claims to be included therein.

---

That which is claimed is:

1. Isolated DNA encoding a $D_{1B}$-dopamine receptor selected from the group consisting of:
   (a) isolated DNA encoding the rat $D_{1B}$-dopamine receptor having the amino acid sequence given in SEQ ID NO:4;
   (b) isolated mammalian DNA which selectively hybridizes to an oligonucleotide probe capable of selectively hybridizing to a DNA comprising a portion of a gene coding for a $D_{1B}$-dopamine receptor having the amino acid sequence given in SEQ ID NO:4, which probe does not hybridize to a gene coding for a $D_{1B}$-dopamine receptor, which isolated mammalian DNA encodes a mammilian $D_{1B}$-dopamine receptor; and
   (c) isolated DNA differing from the isolated DNAs of (a) and (b) above in codon sequence due to the degeneracy of the genetic code, and which encodes a $D_{1B}$-dopamine receptor.

2. Isolated DNA according to claim 1 which encodes rat $D_{1B}$-dopamine receptor.

3. Isolated DNA which encodes the rat $D_{1B}$-dopamine receptor given in SEQ ID NO:4.

4. A recombinant DNA comprising vector DNA and a DNA according to claim 1, 2, or 3.

5. A recombinant DNA according to claim 4, wherein said vector DNA comprises a plasmid.

6. A recombinant DNA according to claim 4, wherein said vector DNA comprises a virus.

7. A recombinant DNA according to claim 4, wherein said vector DNA comprises a baculovirus.

8. A host cell containing a recombinant DNA of claim 4.

9. A host cell containing a recombinant DNA of claim 4 and capable of expressing the encoded $D_{1B}$-dopamine receptor.

10. A host cell according to claim 9, wherein said host cell is a mammalian cell.

11. A host cell according to claim 9, wherein said host cell is an insect cell.

12. An oligonucleotide probe capable of selectively hybridizing to a DNA comprising a portion of a gene coding for a $D_{1B}$-dopamine receptor having the amino acid sequence given in SEQ ID NO:4, which probe does not hybridize to a gene coding for a $D_{1A}$-dopamine receptor.

13. An oligonucleotide probe according to claim 12, which probe is capable of serving as a PCR extension primer.

14. An oligonucleotide probe according to claim 12, which probe is labelled with a detectable group.

15. An oligonucleotide probe according to claim 14, which detectable group is a radioactive atom.

* * * * *

UNITED STATES PATENT AND TRADEMARK OFFICE
CERTIFICATE OF CORRECTION

PATENT NO.   :   5,215,915
DATED         :   June 1, 1993
INVENTOR(S) :  Mario Tiberi, Keith R. Jarvie, Marc G. Caron It is certified that error appears in the above-identified patent and that said Letters Patent is hereby corrected as shown below:

Column 5, Line 45, correct "$D_S$" to read --$D_{1B}$--.

Column 6, Line 4, correct "27" to read --17--.

Column 10, Line 66, correct "D receptor" to read
-- $D_1$ receptor --.

Column 11, Line 4, correct "5-D" to read --5-$D_1$--.

Column 12, Line 22, Example 7 correct "D receptor" to read
-- $D_1$ --.

Column 21, Line 42, Claim 1, correct "$D_{1B}$" to read
-- $D_{1A}$ --.

Signed and Sealed this

Eighth Day of February, 1994

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

AACCATGGAT CCTACATCCC TGTGGCCATC ATGATTGTCA CNTA 4

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:2:

CCNCACAAAC ACACGACAAC CGATGGAAAG AAGCTTAAGA TCAAT            4

( 2 ) INFORMATION FOR SEQ ID NO:3:

( i ) SEQUENCE CHARACTERISTICS:
        ( A ) LENGTH: 2308 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 694..2118
        ( D ) OTHER INFORMATION:

( x i ) SEQUENCE DESCRIPTION: SEQ ID NO:3:

```
GAATTCAAGG TCCTATGACC CAGAATAGGG GTTCGGGATA CAGTTGTGAC TTCGAAGGCC     60

ACTCTCCTAT CCTCTAAGTC TCTGGTTTGT CTAGAGGCCT CTGGATCTCC TCCACCCAGA    120

AGTGTTCCAG GAGAGACACC AAGAGAGGTG TTTGGGAGAA GCTAATTCAT GGGTTTGGGG    180

CAAGGGTGTG GCACTGGGTT CACTCTCGGA CCTGTGTGTG GCCTCTAAAG TTGGAAGAAG    240

ACATCAGAGA GTCATGAAGC TAGGAAGCAG GTGGGAGGGT GCGCGGGCTG CAGAAGCGTG    300

GCTGATAGGG GCGGGCGCGC GGGACGCGGC AGCCACCGCG CCAGAGAGAT CGCCCGGTGC    360

CCGCGACTCC GGACCCCGCC CCCGTTGGCG GCCGCTCTGC GTTTCTCCGA CTCGGAACCA    420

GACACAGTGG CAGCCTCCGG TGTGCTGCCG ACACAGGATC TCAGACCCGG CGGCCCGCGG    480

GCATCGGTCG TTTCTGGTCC CATCTTGGGG ACCAGAGGTG CGCAAGAGTG TTACCATTAC    540

AGGATCCTAA GCGGTGCACG GTGAGCGCTC CTCGGGTCGG GGACGGTCAG CTGCAGGGCC    600

CGGACGACCT CTGGGGTGGC CGATGGGGCC TTCCACGGGG CGCAGGGGCG AAGTTGGGAC    660

CGCAAGCAGA GAGCCCGAGC TACTCAGCGC GAC ATG CTG CCT CCT GGG CGC AAC     714
                                   Met Leu Pro Pro Gly Arg Asn
                                   1               5
```

| | | | | | | | | | | | | | | | | |
|---|---|---|---|---|---|---|---|---|---|---|---|---|---|---|---|---|
| CGC | ACG | GCT | CAA | CCG | GCA | AGG | CTG | GGA | TTA | CAG | AGG | CAA | CTG | GCT | CAG | 762 |
| Arg | Thr | Ala | Gln | Pro | Ala | Arg | Leu | Gly | Leu | Gln | Arg | Gln | Leu | Ala | Gln | |
| | | 10 | | | | 15 | | | | 20 | | | | | | |
| GTG | GAC | GCC | CCA | GCG | GGC | TCT | GCA | ACC | CCA | CTG | GGA | CCC | GCG | CAG | GTG | 810 |
| Val | Asp | Ala | Pro | Ala | Gly | Ser | Ala | Thr | Pro | Leu | Gly | Pro | Ala | Gln | Val | |
| | 25 | | | | 30 | | | | | 35 | | | | | | |
| GTC | ACC | GCA | GGC | CTC | CTG | ACT | CTC | CTA | ATC | GTC | TGG | ACC | TTG | CTC | GGG | 858 |
| Val | Thr | Ala | Gly | Leu | Leu | Thr | Leu | Leu | Ile | Val | Trp | Thr | Leu | Leu | Gly | |
| 40 | | | | | 45 | | | | | 50 | | | | | 55 | |
| AAC | GTG | CTA | GTG | TGT | GCT | GCC | ATC | GTC | CGC | AGC | CGC | CAT | CTG | CGC | GCC | 906 |
| Asn | Val | Leu | Val | Cys | Ala | Ala | Ile | Val | Arg | Ser | Arg | His | Leu | Arg | Ala | |
| | | | 60 | | | | | 65 | | | | | 70 | | | |
| AAG | ATG | ACC | AAC | ATC | TTC | ATC | GTA | TCC | CTA | GCT | GTC | TCA | GAC | CTC | TTC | 954 |
| Lys | Met | Thr | Asn | Ile | Phe | Ile | Val | Ser | Leu | Ala | Val | Ser | Asp | Leu | Phe | |
| | | | 75 | | | | | 80 | | | | | 85 | | | |
| GTG | GCA | TTG | CTG | GTC | ATG | CCC | TGG | AAG | GCT | GTG | GCT | GAG | GTG | GCT | GGG | 1002 |
| Val | Ala | Leu | Leu | Val | Met | Pro | Trp | Lys | Ala | Val | Ala | Glu | Val | Ala | Gly | |
| | | | 90 | | | | 95 | | | | | 100 | | | | |
| TAC | TGG | CCC | TTT | GGG | ACA | TTC | TGC | GAC | ATC | TGG | GTG | GCC | TTT | GAC | ATC | 1050 |
| Tyr | Trp | Pro | Phe | Gly | Thr | Phe | Cys | Asp | Ile | Trp | Val | Ala | Phe | Asp | Ile | |
| | | | 105 | | | | 110 | | | | | 115 | | | | |
| ATG | TGC | TCC | ACT | GCC | TCC | ATC | CTG | AAT | CTG | TGT | ATC | ATC | AGC | GTG | GAC | 1098 |
| Met | Cys | Ser | Thr | Ala | Ser | Ile | Leu | Asn | Leu | Cys | Ile | Ile | Ser | Val | Asp | |

-continued

| | | | | | | | | | | | | | | | | |
|---|---|---|---|---|---|---|---|---|---|---|---|---|---|---|---|---|
| 120 | | | | | 125 | | | | | 130 | | | | | 135 | |

CGT TAC TGG GCT ATT TCC AGA CCC TTC CGC TAC GAG CGC AAG ATG ACC    1146
Arg Tyr Trp Ala Ile Ser Arg Pro Phe Arg Tyr Glu Arg Lys Met Thr
            140             145                 150

CAG CGA GTA GCC CTG GTC ATG GTG GGC CTG GCC TGG ACC TTG TCC ATC    1194
Gln Arg Val Ala Leu Val Met Val Gly Leu Ala Trp Thr Leu Ser Ile
                155             160                 165

CTC ATC TCC TTC ATC CCG GTC CAA CTC AAT TGG CAC AGA GAC AAG GCA    1242
Leu Ile Ser Phe Ile Pro Val Gln Leu Asn Trp His Arg Asp Lys Ala
            170             175                 180

GGC TCC CAG GGC CAA GAG GGC CTG CTG TCC AAT GGG ACA CCC TGG GAG    1290
Gly Ser Gln Gly Gln Glu Gly Leu Leu Ser Asn Gly Thr Pro Trp Glu
        185             190                 195

GAA GGC TGG GAG CTA GAA GGG AGG ACG GAG AAC TGT GAC TCC AGC CTG    1338
Glu Gly Trp Glu Leu Glu Gly Arg Thr Glu Asn Cys Asp Ser Ser Leu
200             205                 210             215

AAC CGA ACC TAT GCC ATC TCC TCG TCA CTC ATC AGC TTC TAC ATC CCG    1386
Asn Arg Thr Tyr Ala Ile Ser Ser Ser Leu Ile Ser Phe Tyr Ile Pro
            220                 225             230

GTG GCC ATC ATG ATC GTG ACC TAT ACG CGT ATC TAC CGC ATT GCG CAG    1434
Val Ala Ile Met Ile Val Thr Tyr Thr Arg Ile Tyr Arg Ile Ala Gln
                235             240                 245

GTG CAG ATC CGG CGG ATC TCC TCC CTA GAG AGG GCA GCT GAG CAT GCT    1482
Val Gln Ile Arg Arg Ile Ser Ser Leu Glu Arg Ala Ala Glu His Ala
            250             255                 260

CAG AGT TGC CGG AGT CGT GGA GCC TAT GAA CCT GAC CCC AGC CTG CGA    1530
Gln Ser Cys Arg Ser Arg Gly Ala Tyr Glu Pro Asp Pro Ser Leu Arg
        265             270                 275

GCG TCC ATC AAG AAG GAG ACC AAG GTC TTC AAA ACC CTG TCA ATG ATC    1578
Ala Ser Ile Lys Lys Glu Thr Lys Val Phe Lys Thr Leu Ser Met Ile
280             285                 290             295

ATG GGG GTC TTC GTG TGT TGC TGG TTG CCT TTC TTC ATC CTG AAC TGT    1626
Met Gly Val Phe Val Cys Cys Trp Leu Pro Phe Phe Ile Leu Asn Cys
            300                 305             310

ATG GTT CCT TTC TGC AGT AGT GGG GAT GCC GAG GGC CCA AAG ACT GGC    1674
Met Val Pro Phe Cys Ser Ser Gly Asp Ala Glu Gly Pro Lys Thr Gly
            315             320                 325

TTC CCT TGT GTC AGC GAG ACC ACC TTC GAC ATA TTC GTC TGG TTT GGC    1722
Phe Pro Cys Val Ser Glu Thr Thr Phe Asp Ile Phe Val Trp Phe Gly
        330             335                 340

TGG GCG AAC TCC TCT CTC AAT CCC ATC ATC TAT GCC TTT AAT GCA GAC    1770
Trp Ala Asn Ser Ser Leu Asn Pro Ile Ile Tyr Ala Phe Asn Ala Asp
345             350                 355

TTC CGG AAG GTG TTT GCC CAG CTG CTG GGG TGC AGC CAC TTC TGC TTC    1818
Phe Arg Lys Val Phe Ala Gln Leu Leu Gly Cys Ser His Phe Cys Phe
360             365                 370             375

CGG ACC CCA GTG CAG ACG GTA AAC ATC AGT AAT GAG CTC ATC TCC TAC    1866
Arg Thr Pro Val Gln Thr Val Asn Ile Ser Asn Glu Leu Ile Ser Tyr
            380             385                 390

AAC CAA GAC ACG GTC TTC CAC AAG GAG ATC GCT ACT GCC TAT GTC CAC    1914
Asn Gln Asp Thr Val Phe His Lys Glu Ile Ala Thr Ala Tyr Val His
            395             400             405

ATG ATA CCG AAT GCA GTA TCC TCC GGA GAC AGG GAG GTG GGA GAG GAG    1962
Met Ile Pro Asn Ala Val Ser Ser Gly Asp Arg Glu Val Gly Glu Glu
            410             415                 420

GAG GAG GAG GGG CCT TTC GAT CAC ATG TCT CAA ATC TCT CCA ACG ACG    2010
Glu Glu Glu Gly Pro Phe Asp His Met Ser Gln Ile Ser Pro Thr Thr
425             430                 435

CCA GAC GGT GAC CTG GCT GCT GAG TCT GTC TGG GAG CTT GAC TGT GAG    2058
Pro Asp Gly Asp Leu Ala Ala Glu Ser Val Trp Glu Leu Asp Cys Glu
440             445                 450             455

-continued

```
GAA  GAG  GTT  TCC  TTA  GGC  AAA  ATC  TCA  CCT  CTC  ACC  CCC  AAT  TGT  TTC                    2106
Glu  Glu  Val  Ser  Leu  Gly  Lys  Ile  Ser  Pro  Leu  Thr  Pro  Asn  Cys  Phe
                         460                 465                      470

GAT  AAA  ACT  GCT  TAGAAACATT  CTCATGGGCA  TATACAATGG  TGGCCATATT                                  2158
Asp  Lys  Thr  Ala
               475

TCCAAGCATG  CACAAATACC  CACGTGCGTA  CACACACACA  CACACACACA  CACACACACA                              2218

CACACACTCC  AGTGTGCATA  TGCTTTCTGT  AGTCTGCTGC  ATAGAAACAA  ACGATTCTTA                              2278

GCTGAGAAAT  GACGAGGCTG  TTGGATAACT                                                                  2308
```

( 2 ) INFORMATION FOR SEQ ID NO:4:

( i ) SEQUENCE CHARACTERISTICS:
        ( A ) LENGTH: 475 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Leu  Pro  Pro  Gly  Arg  Asn  Arg  Thr  Ala  Gln  Pro  Ala  Arg  Leu  Gly
 1                   5                        10                       15

Leu  Gln  Arg  Gln  Leu  Ala  Gln  Val  Asp  Ala  Pro  Ala  Gly  Ser  Ala  Thr
               20                   25                        30

Pro  Leu  Gly  Pro  Ala  Gln  Val  Val  Thr  Ala  Gly  Leu  Leu  Thr  Leu  Leu
          35                        40                        45

Ile  Val  Trp  Thr  Leu  Leu  Gly  Asn  Val  Leu  Val  Cys  Ala  Ala  Ile  Val
     50                        55                        60

Arg  Ser  Arg  His  Leu  Arg  Ala  Lys  Met  Thr  Asn  Ile  Phe  Ile  Val  Ser
 65                       70                       75                        80

Leu  Ala  Val  Ser  Asp  Leu  Phe  Val  Ala  Leu  Leu  Val  Met  Pro  Trp  Lys
                    85                        90                        95

Ala  Val  Ala  Glu  Val  Ala  Gly  Tyr  Trp  Pro  Phe  Gly  Thr  Phe  Cys  Asp
               100                      105                      110

Ile  Trp  Val  Ala  Phe  Asp  Ile  Met  Cys  Ser  Thr  Ala  Ser  Ile  Leu  Asn
          115                      120                      125

Leu  Cys  Ile  Ile  Ser  Val  Asp  Arg  Tyr  Trp  Ala  Ile  Ser  Arg  Pro  Phe
     130                      135                      140

Arg  Tyr  Glu  Arg  Lys  Met  Thr  Gln  Arg  Val  Ala  Leu  Val  Met  Val  Gly
145                      150                      155                      160

Leu  Ala  Trp  Thr  Leu  Ser  Ile  Leu  Ile  Ser  Phe  Ile  Pro  Val  Gln  Leu
                    165                      170                      175

Asn  Trp  His  Arg  Asp  Lys  Ala  Gly  Ser  Gln  Gly  Gln  Glu  Gly  Leu  Leu
               180                      185                      190

Ser  Asn  Gly  Thr  Pro  Trp  Glu  Glu  Gly  Trp  Glu  Leu  Glu  Gly  Arg  Thr
          195                      200                      205

Glu  Asn  Cys  Asp  Ser  Ser  Leu  Asn  Arg  Thr  Tyr  Ala  Ile  Ser  Ser  Ser
     210                      215                      220

Leu  Ile  Ser  Phe  Tyr  Ile  Pro  Val  Ala  Ile  Met  Ile  Val  Thr  Tyr  Thr
225                      230                      235                      240

Arg  Ile  Tyr  Arg  Ile  Ala  Gln  Val  Gln  Ile  Arg  Arg  Ile  Ser  Ser  Leu
                    245                      250                      255

Glu  Arg  Ala  Ala  Glu  His  Ala  Gln  Ser  Cys  Arg  Ser  Arg  Gly  Ala  Tyr
               260                      265                      270

Glu  Pro  Asp  Pro  Ser  Leu  Arg  Ala  Ser  Ile  Lys  Lys  Glu  Thr  Lys  Val
          275                      280                      285

Phe  Lys  Thr  Leu  Ser  Met  Ile  Met  Gly  Val  Phe  Val  Cys  Cys  Trp  Leu
     290                      295                      300
```

```
Pro  Phe  Phe  Ile  Leu  Asn  Cys  Met  Val  Pro  Phe  Cys  Ser  Ser  Gly  Asp
305                      310                     315                      320

Ala  Glu  Gly  Pro  Lys  Thr  Gly  Phe  Pro  Cys  Val  Ser  Glu  Thr  Thr  Phe
                    325                     330                      335

Asp  Ile  Phe  Val  Trp  Phe  Gly  Trp  Ala  Asn  Ser  Ser  Leu  Asn  Pro  Ile
               340                     345                     350

Ile  Tyr  Ala  Phe  Asn  Ala  Asp  Phe  Arg  Lys  Val  Phe  Ala  Gln  Leu  Leu
          355                     360                     365

Gly  Cys  Ser  His  Phe  Cys  Phe  Arg  Thr  Pro  Val  Gln  Thr  Val  Asn  Ile
     370                     375                     380

Ser  Asn  Glu  Leu  Ile  Ser  Tyr  Asn  Gln  Asp  Thr  Val  Phe  His  Lys  Glu
385                      390                     395                      400

Ile  Ala  Thr  Ala  Tyr  Val  His  Met  Ile  Pro  Asn  Ala  Val  Ser  Ser  Gly
                    405                     410                     415

Asp  Arg  Glu  Val  Gly  Glu  Glu  Glu  Glu  Gly  Pro  Phe  Asp  His  Met
               420                     425                     430

Ser  Gln  Ile  Ser  Pro  Thr  Thr  Pro  Asp  Gly  Asp  Leu  Ala  Ala  Glu  Ser
          435                     440                     445

Val  Trp  Glu  Leu  Asp  Cys  Glu  Glu  Glu  Val  Ser  Leu  Gly  Lys  Ile  Ser
450                      455                     460

Pro  Leu  Thr  Pro  Asn  Cys  Phe  Asp  Lys  Thr  Ala
465                      470                     475
```